United States Patent [19]

Ogiu

[11] 4,367,729

[45] Jan. 11, 1983

[54] ENDOSCOPE PROVIDED WITH AN ELONGATE MEDICAL TREATING INSTRUMENT UTILIZING LASER BEAMS

[75] Inventor: Hisao Ogiu, Oume, Japan

[73] Assignee: Olympus Optical Co. Ltd., Tokyo, Japan

[21] Appl. No.: 197,806

[22] Filed: Oct. 17, 1980

[30] Foreign Application Priority Data

Oct. 22, 1979 [JP] Japan .......................... 54-146156[U]

[51] Int. Cl.$^3$ ............................................. A61B 1/06
[52] U.S. Cl. ........................................................ 128/6
[58] Field of Search ............................................ 128/6

[56] References Cited

U.S. PATENT DOCUMENTS

| | | | |
|---|---|---|---|
| 3,155,761 | 11/1964 | Rubens et al. | 128/6 |
| 3,494,364 | 2/1970 | Peters | 128/303.17 |
| 3,941,121 | 3/1976 | Olinger et al. | 128/6 |
| 4,043,342 | 8/1977 | Morrison | 128/303.17 |
| 4,072,147 | 2/1978 | Hett | 128/6 |
| 4,167,943 | 9/1979 | Banko | 128/6 |
| 4,167,944 | 9/1979 | Banko | 128/6 |
| 4,273,109 | 6/1981 | Enderby | 128/6 |
| 4,286,585 | 9/1981 | Ogawa | 128/6 |

FOREIGN PATENT DOCUMENTS 2902829 8/1979 Fed. Rep. of Germany .......... 128/6

Primary Examiner—Kyle L. Howell
Assistant Examiner—Daniel P. Burke

[57] ABSTRACT

An endoscope embodying this invention comprises a control section, an elongate flexible insertion section having one end connected to the control section and the other constituting a distal end part, a transparent glass cover member mounted in the front end face of the distal end part, a channel extending through both the control section and insertion section, an elongate laser guide which extends through the channel and has one end pressed against the rear face of the glass cover member and the other end is connected to a laser oscillator disposed outside of the endoscope, an urging member holder mounted on the control section, and an elastic urging member received in the holder and urging the laser guide toward the glass cover member.

Application of the elastic urging member enables the distal end face of the laser guide to be always pressed against the rear face of the glass cover member, no matter how much the bend portion of the endoscope may be flexed. Therefore, the endoscope has the advantages that it is possible to prevent the burning damage of the channel and the emission of laser beams on the inner wall of the channel due to the Fresnel reflection resulting from the fall-off of the distal end face of the laser guide from the glass cover member, and the distal end face of the laser guide is rigidly pressed against the glass cover member, thereby preventing the breakage of the distal end face of the laser guide and glass cover member or the fall-off of the glass cover member from the distal end part of the endoscope.

6 Claims, 5 Drawing Figures

ENDOSCOPE PROVIDED WITH AN ELONGATE MEDICAL TREATING INSTRUMENT UTILIZING LASER BEAMS

This invention relates to an endoscope provided with an elongated medical treating instrument utilizing laser beams.

Already known is an endoscope wherein a laser guide is inserted into a channel formed in the endoscope, and laser beams transmitted through the laser guide are emitted from the endoscope distal end to effect the excision or hemostasis of an affected part of, for example, a patient's coeliac cavity. With the prior art endoscope of the above-mentioned type, the laser guide is inserted into the channel, until the guide reaches the rear face of a glass cover member mounted on the distal end of the channel. Since the insertion section of the endoscope contains a light guide and other parts, the channel is generally displaced from the axis of the insertion section. Where, therefore, the insertion section is kept straight, the distal end face of the laser guide contacts the glass cover member. Where, however, the insertion section is bent with a small curvature, and the channel is positioned in the outer part of the bent portion, the channel is elongated, sometimes causing the distal end face of the laser guide to fall off the rear face of the glass cover member. At this event, laser beams emitted from the distal end of the laser guide are directly irradiated on the inner wall of the channel or reflected by the glass cover member, leading to a decline in irradiation efficiency of laser beams and undesirable irradiation of the reflected laser beams on the inner wall of the channel. Further, heat generated by the reflected laser beams emitted on the inner wall of the channel is likely to damage not only the channel but also the endoscope itself.

The object of this invention is to provide an endoscope which enables the distal end face of a laser guide to be always pressed against the rear end face the glass cover member, thereby ensuring improvement on the irradiation efficiency of laser beams and the prevention of the damage of not only the channel but also the endoscope itself due to emission of the laser beams on the inner wall of an endoscope channel through which the laser guide extends.

To attain the above-mentioned object, this invention provides an endoscope which comprises a control section, an elongate flexible insertion section, one end of which is connected to the control section, and the other end of which is connected by a distal end part, a transparent glass cover member fixedly mounted in the front face of the distal end part, a channel extending through the control section and distal end part, an elongate laser guide which extends through the channel, the distal end of which is pressed against the rear face of the glass cover member, and the proximal end of which is connected to a laser oscillator provided outside of the endoscope, a holder mounted on the control section, and elastic urging means which is supported by the holder and urging the laser guide toward the glass cover member.

The laser guide may be provided with stop means which is adjusted axially of the laser guide.

Application of elastic urging means enables the distal end face of the laser guide to be always pressed against the rear face of the glass cover member, no matter how much the sheath and bend portion of the endoscope may be flexed, offering the advantages that it is possible to prevent the burning of the channel and the emission of laser beams on the inner wall of the channel due to the Fresnel reflection resulting from the fall off of the distal end face of the laser guide from the glass cover member; the distal end face of the laser guide and the glass cover member are saved from damage due to the fact that the distal end face is pressed too strongly against the glass cover member; and the glass cover member is prevented from falling off the distal end part of the insertion section of the endoscope.

Further advantages of an endoscope embodying this invention are that when the stop means are adjustable axially of the laser guide, an error in fitting the stop means to the laser guide can be compensated; and the force with which the laser guide urges the stop means toward the glass cover member can be adjusted.

This invention can be understood from the detailed description with reference to the accompanying drawings, in which.

Figure 1:
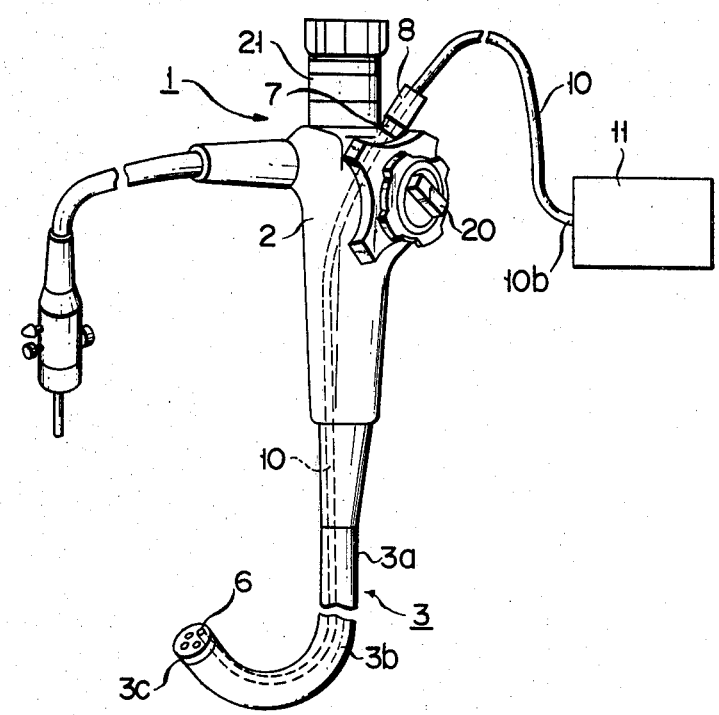
FIG. 1 shows the whole view of an endoscope embodying this invention.
Figure 2:
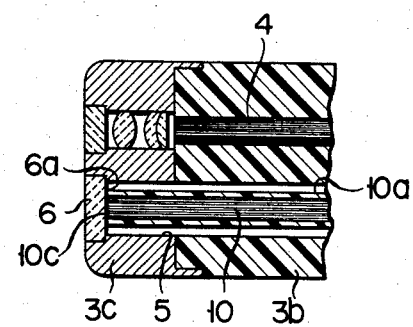
FIG. 2 is a longitudinal sectional view of the distal end section of the endoscope embodying this invention.
Figure 4:
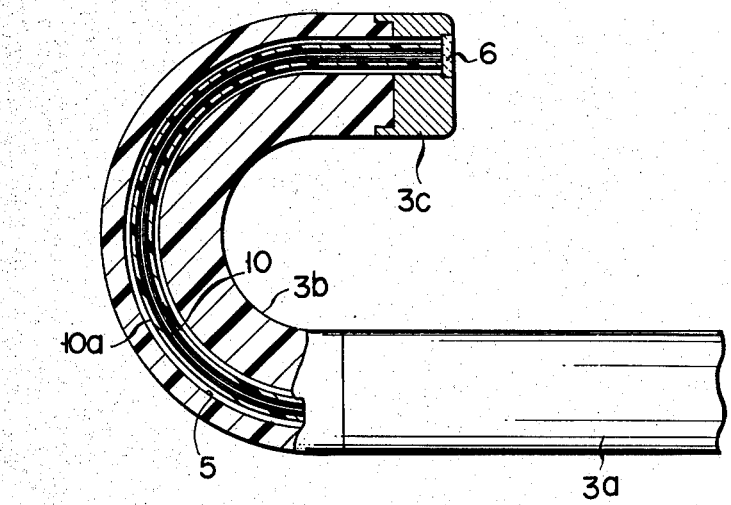
FIG. 4 shows the condition in which the distal end face of the laser guide is pressed against the glass cover member even when the bend section of the endoscope is flexed.

Referring to FIG. 1, an endoscope 1 comprises a control section 2 and an elongate insertion section 3, one end of which is fixed to one end of the control section 2 and which is inserted into a desired portion of a coeliac cavity of, for example, a human body. The insertion section 3 is formed of a series of a flexible sheath 3a fixed to the control section 2, a flexible bend part 3b and a rigid distal end part 3c (FIGS. 1, 2 and 4).

Referring to FIGS. 1 to 4, the insertion section 3 contains an image guide or image-transmitting element 4, light guide which receives a light from a light source (not shown) provided outside of an endoscope and other penetrating members. A channel 5 for the insertion of a laser guide also extends through the insertion section 3, and further through the control section 2 to communicate with a hollow cylindrical laser guide inlet 7 which is fitted to the other end of the control section 2. Threadedly engaged with the outer end of the laser guide inlet 7 is one end of a hollow cylindrical holder 8, the other end of which is constituted by an end wall 8a. A transparent disc-shaped glass cover member 6 is fixedly mounted in the front end wall of the distal end part 3c.

A laser guide 10 extends through the channel 5, light guide inlet 7 and the hollow cylindrical holder 8. The laser guide 10 comprises, for example, an optical fiber and a guide tube 10a enclosing the fiber. Obviously, the laser guide 10 may be formed of a flexible optical laser transmission element of a different construction. That end 10b of the laser guide 10 which protrudes from the holder 8 is connected to a laser oscillator 11. The other end 10c of the laser guide 10 extends up to the rear face 6a of the glass cover member 6.

Figure 3:
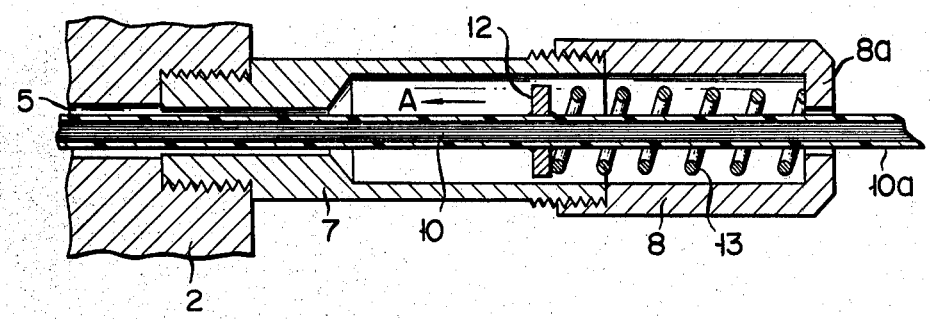
FIG. 3 is a longitudinal sectional view of the main part of an endoscope according to one embodiment of the invention.

Referring to FIG. 3, a ring-shaped stop 12 is securely mounted on the laser guide 10 in the light guide inlet 7 and/or holder 8. Provided in the holder 8 is a compression coil spring 13 which surrounds the laser guide 10, one end of which is pressed against the inner face of the end wall 8a, and the other end of which is pressed against that side of the stop 12 which faces the end wall 8a such that the compression coil spring 13 urges the laser guide 10 toward the glass cover member 6, thereby causing the other end (distal end) 10c of the laser guide 10 to be always pressed against the rear face 6a of the glass cover member 6.

A knob 20 is provided on one of the side walls of the control section 2 to control the flexing of the bend part 3b. The rotation of the knob 20 adjusts the extent to which the bend part 3b is to be flexed by means of wires (not shown) extending through the insertion section 3 like the conventional endoscope. An ocular 21 optically connected to an image guide 4 is provided at said one end of the control section 2. The other parts of the endoscope 1 are constructed in the same manner as those of the prior art endoscope (as set forth in the specification of the U.S. Pat. Nos. 3,858,577 and 4,072,147). Description is omitted of said other parts which fall outside of the object and scope of this invention. Referring to FIGS. 2 and 4, the bend part 3b of the endoscope 1 is indicated in the solid form for brief of description, but is constructed in the same manner as that of the conventional endoscope.

In operation, the operator puts the insertion section 3 of the endoscope 1 into a prescribed part of a coeliac cavity of, for example, a patient. The operator observes the coeliac cavity through the light guide 10, image guide 4 and ocular 21, and directs the glass cover member 6 toward an affected part of the coeliac cavity. Then, the laser oscillator is actuated. Laser beams emitted from the laser oscillator 11 pass through the laser guide 11 and glass cover member 6 to illuminate the affected part of the coeliac cavity, allowing for the excision or hemostasis of the affected part.

With the foregoing embodiment, the laser guide 10 is always urged toward the distal end of the channel 5, that is, toward the glass cover member 6 by the urging force of the compression coil spring 13. Where, as shown in FIG. 4, the insertion section 3 of the endoscope 1 is flexed with a small radius of curvature in case the channel 5 is in the outer part of the insertion section 3, the compression coil spring 13 is elongated to an extent corresponding to said extension of the channel 5. As a result, the laser guide 10 is slidable through the channel 5 in the direction of an arrow A shown in FIG. 5 and the reverse direction, enabling the distal end face 10c of the laser guide 10 to be tightly pressed against the rear face 6a of the glass cover member 6. Conversely where the insertion section 3 of the endoscope 1 is flexed with the channel 5 set inside of the insertion section 3, the channel 5 is forcefully contracted with a decrease in its length. In this case, the compression coil spring 13 is compressed to an extent corresponding to said contraction of the channel 5, causing the laser guide 10 to be moved outward. Therefore, the glass cover member 6 is prevented from being subjected to an excess stress. This arrangement offers the advantage of enabling the insertion section 3 to be smoothly flexed and saving the glass cover member 6 from breakage.

The distal end face 10c of the laser guide 10 is tightly pressed against the glass cover member 6. Where, therefore, the distal end face 10c is set exactly perpendicular to the optical axis of the laser guide 10, the whole and close contact of the distal end face 10c with the glass cover member 6 enables the optical axis of the laser guide 10 to be automatically set perpendicular to the rear face 6a of the glass cover member 6. Consequently, the Fresnel reflection at the rear face 6a of the glass cover member 6 is minimized, thereby elevating the irradiation efficiency of laser beams.

Figure 5:
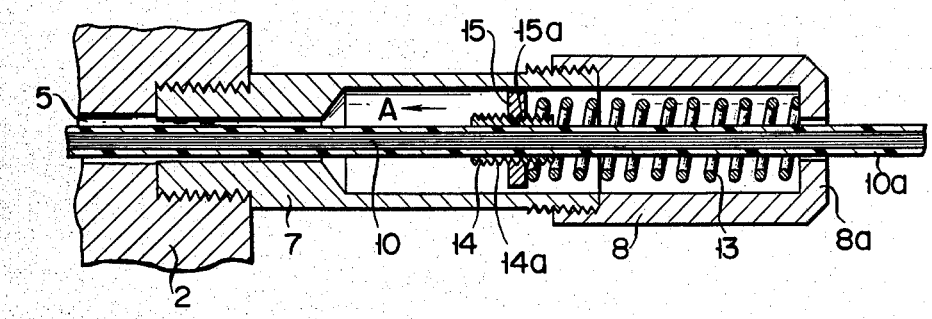
FIG. 5 is a longitudinal sectional view of the main part of an endoscope according to another embodiment of the invention.

Description is now given with reference to FIG. 5 of an endoscope according to a second embodiment of this invention. A hollow cylindrical stop position-adjusting member 14 is securely mounted on the laser guide 10 in the light guide inlet 7 and/or hollow cylindrical holder 8. External screw threads 14a are provided on the outer peripheral wall of the stop position-adjusting member 14. Internal screw threads 15a formed in a ring-shaped stop 15 are engaged with the external screw threads 14a of the stop position-adjusting member 14. The axial movement of the stop position-adjusting member 14 is controlled by rotating the ring-shaped stop 15. Where, therefore, laser guide 10 is insufficiently inserted into the channel 5 and the distal end face 10c of the laser guide 10 does not reach the rear face 6a of the glass cover member 6 or conversely where the laser guide 10 is inserted into the channel 5 in excess, causing the distal end face 10c of the laser guide 10 to push the glass cover member 6 with an unduly great force, the resultant difficulties can be resolved by adjusting the position of the ring-shaped stop 15. Therefore, the distal end face 10c of the laser guide 10 can be always pressed against the rear face 6a of the glass cover member 6 with a proper urging force of the compression coil spring 13.

With the foregoing embodiments, a compression coil spring was used as an urging member. Obviously, any other type of an urging member formed of, for example, elastic rubber is applicable.

With an endoscope embodying this invention which is constructed as described above, the laser guide is urged toward the distal end of the laser guide by the urging member to let the distal end face of the laser guide be pressed against the rear face of the glass cover member. Even where, therefore, the insertion section of the endoscope is flexed in various directions, the distal end face of the laser guide is prevented from falling off the rear face of the glass cover member, preventing the Fresnel reflection on the rear face of the glass cover member obviously with an increase in the irradiation efficiency of laser beams. With the endoscope of this invention, therefore, the channel or endoscope itself can be saved from damage resulting from the direct illumination of the inner wall of the channel by laser beams or the Fresnel reflection at the rear face of the glass cover member.

What is claimed is:

1. An endoscope provided with an elongate medical treating instrument utilizing laser beams comprising:
   a control section having two ends;
   an elongate flexible insertion section having two ends, one of which is fixed to one of said two ends of said control section, and the other of which constitutes a distal end part and is provided with a distal end face;
   a transparent glass cover member which is mounted in said distal end face of said distal end part and has a rear face;
   a channel extending through said control section and said insertion section;

an elongate laser guide which extends through said channel and has two ends, one of which is connected to a laser oscillator provided outside of said endoscope and stop means provided on said laser guide a holder mounted on the other end of the control section and having an end wall; and an elastically expansible member disposed in said holder between said stop means and the end wall of said holder to urge the laser guide toward said other end of said insertion section of said endoscope and cause the other end of the laser guide to tightly abut against said rear face of said glass cover member no matter how much said insertion section is bent.

2. The endoscope according to claim 1, wherein said stop means is a ring-shaped stop fixedly mounted on said laser guide.

3. The endoscope according to claim 2, wherein said elastically expansible member is a helical coil spring surrounding said laser guide.

4. The endoscope according to claim 1, wherein said stop means comprises:
a hollow cylindrical stop position-adjusting member which is securely mounted on said laser guide and provided with external screw threads; and
a ring-shaped stop which is provided with internal screw threads and threadably engaged with said stop position-adjusting member.

5. The endoscope according to claim 4, wherein said elastically expansible member is a helical coil spring surrounding the laser guide.

6. The endoscope according to any of claims 2 to 5, further comprising a hollow cylindrical laser guide inlet which has two ends, one of which is connected to said one end of said holder, and the other of which is connected to the other end of said control section of said endoscope for communication with said channel, and through which said laser guide extends.

* * * * *